United States Patent
Ramarajan et al.

(10) Patent No.: US 8,706,521 B2
(45) Date of Patent: *Apr. 22, 2014

(54) TREATMENT RELATED QUANTITATIVE DECISION ENGINE

(76) Inventors: Naresh Ramarajan, Tujunga, CA (US); Gitika Srivastava, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/183,757

(22) Filed: Jul. 15, 2011

(65) Prior Publication Data

US 2012/0016690 A1 Jan. 19, 2012

Related U.S. Application Data

(60) Provisional application No. 61/364,973, filed on Jul. 16, 2010.

(51) Int. Cl.
*G06Q 50/00* (2012.01)

(52) U.S. Cl.
USPC .......................................................... 705/2

(58) Field of Classification Search
None
See application file for complete search history.

(56) References Cited

U.S. PATENT DOCUMENTS

| | | | | |
|---|---|---|---|---|
| 6,049,794 | A | 4/2000 | Jacobs et al. | 706/45 |
| 6,581,038 | B1 | 6/2003 | Mahran | 705/3 |
| 6,584,445 | B2 * | 6/2003 | Papageorge | 705/3 |
| 7,548,917 | B2 | 6/2009 | Nelson | 707/7 |
| 7,593,913 | B2 | 9/2009 | Wang et al. | 706/62 |
| 7,707,206 | B2 | 4/2010 | Encina et al. | 707/716 |
| 7,769,600 | B2 | 8/2010 | Iliff | 705/2 |
| 7,805,385 | B2 | 9/2010 | Steck et al. | 706/10 |
| 7,831,444 | B2 | 11/2010 | Brown et al. | 705/2 |
| 7,849,400 | B2 | 12/2010 | Ritter et al. | 715/234 |
| 7,945,454 | B2 | 5/2011 | Firozvi | 705/2 |
| 7,945,497 | B2 | 5/2011 | Kenefick et al. | 705/35 |
| 2003/0088365 | A1 | 5/2003 | Becker | 702/19 |

(Continued)

FOREIGN PATENT DOCUMENTS

| | | | |
|---|---|---|---|
| KR | 10-2009-0072550 | 7/2009 | G06Q 50/00 |
| WO | WO 01/75728 | 10/2001 | G06F 17/60 |

(Continued)

OTHER PUBLICATIONS

International Searching Report—International Application No. PCT/US2011/044190, dated Feb. 29, 2012, together with the Written Opinion of the International Searching Authority, 12 pages.

*Primary Examiner* — John Pauls
*Assistant Examiner* — Jason Tiedeman
(74) *Attorney, Agent, or Firm* — Sunstein Kann Murphy & Timbers LLP

(57) ABSTRACT

A system and method generate a report to help decide among a plurality of treatment options for a medical condition. The system and method receive patient information and generate a plurality of potential treatment options for the medical condition. The system and method also receive the patient's preference(s) for potential treatment outcomes of the treatment options, used to produce a preference value. The system and method also analyze indexed study data relating to the plurality of treatment options to produce, based on the analysis, a study score for each of the treatment options. For each treatment option, the system and method produce a treatment score based on at least the preference value and the study score, thus permitting generation of a report listing the treatment options and a) the treatment scores or b) the information derived from the treatment scores.

41 Claims, 4 Drawing Sheets

(56) References Cited

U.S. PATENT DOCUMENTS

| | | | |
|---|---|---|---|
| 2003/0163353 A1 | 8/2003 | Luce et al. | 705/2 |
| 2003/0229513 A1 | 12/2003 | Spertus | 705/2 |
| 2008/0172214 A1 | 7/2008 | Col et al. | 703/11 |
| 2009/0030945 A1 | 1/2009 | Miller et al. | 707/104.1 |
| 2009/0043733 A1 | 2/2009 | Kingsford et al. | 707/3 |
| 2009/0083075 A1 | 3/2009 | Henschke et al. | 705/3 |
| 2009/0119330 A1 | 5/2009 | Sampath et al. | 707/102 |
| 2009/0144092 A1 | 6/2009 | Vardy | 705/3 |
| 2009/0164237 A1 | 6/2009 | Hunt et al. | 705/2 |
| 2009/0177493 A1 | 7/2009 | Narayan | 705/3 |
| 2009/0177920 A1 | 7/2009 | Richards et al. | 714/15 |
| 2009/0216807 A1 | 8/2009 | Roberts et al. | 707/104.1 |
| 2009/0299766 A1* | 12/2009 | Friedlander et al. | 705/2 |
| 2010/0138199 A1 | 6/2010 | Soto et al. | 703/2 |
| 2010/0145720 A1 | 6/2010 | Reiner | 705/2 |
| 2010/0179831 A1 | 7/2010 | Brown et al. | 705/3 |
| 2010/0191071 A1* | 7/2010 | Anderson et al. | 600/301 |
| 2010/0205006 A1 | 8/2010 | Bergh | 705/3 |
| 2010/0217736 A1 | 8/2010 | Sarel | 706/47 |
| 2010/0217738 A1 | 8/2010 | Sarel | 706/47 |
| 2010/0241454 A1 | 9/2010 | Firminger et al. | 705/3 |
| 2010/0241595 A1 | 9/2010 | Felsher | 705/400 |
| 2010/0287213 A1 | 11/2010 | Rolls et al. | 707/803 |
| 2011/0093288 A1 | 4/2011 | Soto et al. | 705/2 |
| 2011/0112860 A1 | 5/2011 | Kehr | 705/2 |
| 2012/0016206 A1 | 1/2012 | Ramarajan et al. | 600/300 |

FOREIGN PATENT DOCUMENTS

| | | | |
|---|---|---|---|
| WO | WO 01/98866 | 12/2001 | |
| WO | WO 03/021511 | 3/2003 | G06F 17/60 |
| WO | WO 2005/034001 | 4/2005 | G06F 19/00 |
| WO | WO 2009/103156 | 8/2009 | G06F 19/00 |

* cited by examiner

DECISION BOARD

| TREATMENT CHOICE | SIDE EFFECTS | RESULTS OF TREATMENT CHOICE | |
|---|---|---|---|
| | | For Breast | For Survival |
| MASTECTOMY *(Surgical Removal of the Breast)*<br>• Entire breast will be removed<br>• Some lymph nodes under your arm will be removed<br>• You are left with a healing scar that runs across your chest<br>• A drain is inserted near the scar under the arm, for 5-10 days, to remove excess fluid<br>• After surgery, you may be referred to the Cancer Centre for consideration of other treatments (hormonal therapy or chemotherapy)<br>• Radiation is not normally required | MASTECTOMY<br>*OFTEN*<br>• Numbness and discomfort on the inside of the arm where the nerves were cut<br>• Pain, discomfort or numbness of the chest<br>*SOMETIMES*<br>• Stiffness of the shoulder<br>• Collection of fluid in the scar that may need to be drained<br>*RARELY*<br>• Infection<br>• Arm swelling | MASTECTOMY<br>• Healed scar across your chest<br>• Some women may be upset by the loss of their breast<br>• A breast prosthesis or breast form can be fitted<br>• A breast can be reconstructed using plastic surgery<br>• Cancer may come back on the chest. About 5 to 10 out of 100 women will experience this in the next 10 years<br>• Cancer that comes back on the chest is usually treated by surgery, radiation, or both | *MASTECTOMY*<br>*Your chance of surviving cancer is the SAME as with Lumpectomy plus Radiation* |
| LUMPECTOMY *(Surgical Removal of the Cancerous Lump)*<br>• Only the cancerous lump and some surrounding tissue will be removed<br>• Some of the lymph nodes under your arm will be removed<br>• You are left with two healing scars, one on the breast and one under the arm<br>• Often, a drain is inserted near the scar under the arm, for 5-10 days, to remove excess fluid<br>• In some instances (in about 1 out of 10 women), all the cancer in the breast may not be removed and you may require further surgery<br>• Once the breast has healed, 3-4 weeks after surgery, you will be referred to the Cancer Centre for consideration of radiation<br>PLUS<br>RADIATION *(X-ray Treatment)*<br>• You will need to come to the Cancer Centre for planning of the radiation and for treatments<br>• Your treatments will be daily for 5 weeks, excluding weekends<br>• Each visit lasts approximately 30 to 45 minutes<br>• The time between your surgery and the beginning of your radiation treatments may be 6-12 weeks<br>• Other treatments (hormonal therapy and chemotherapy) may be considered<br>• If you are treated with chemotherapy, your radiation will begin after chemotherapy | LUMPECTOMY<br>*OFTEN*<br>• Numbness and discomfort on the inside of the arm where the nerves were cut<br>• Pain, discomfort or numbness of the chest<br>*SOMETIMES*<br>• Stiffness of the shoulder<br>• Collection of fluid in the scar that may need to be drained<br>*RARELY*<br>• Infection<br>• Arm swelling<br>PLUS<br>RADIATION<br>*OFTEN*<br>• Redness of the skin like a sunburn<br>*SOMETIMES*<br>• Increased tiredness<br>• Tanning of the skin<br>• Slight increase in the size of the breast<br>• Slight increase in the firmness of the breast<br>*RARELY*<br>• Blood vessels may become visible on small areas of the skin<br>• Pneumonia | LUMPECTOMY PLUS RADIATION<br>• Two healed scars, one on the breast and one under the arm<br>• Some indentation where the lump was removed or thickening of the breast tissue<br>• Some women may be upset by the way the breast looks, but most (8 out of 10) are satisfied<br>• Cancer may come back in the breast. About 5 to 10 out of 100 women will experience this in the next 10 years<br>• Cancer that comes back in the breast is usually removed by further surgery (lumpectomy or mastectomy). Radiation cannot be given again | *LUMPECTOMY PLUS RADIATION*<br>*Your chance of surviving cancer is the SAME as with Mastectomy* |

*FIG. 3B*

TREATMENT RELATED QUANTITATIVE DECISION ENGINE

PRIORITY

This patent application claims priority from provisional U.S. patent application No. 61/364,973, filed Jul. 16, 2010, entitled, "QUANTITATIVE TREATMENT DECISION ENGINE," and naming Naresh Ramarajan and Gitika Srivastava as inventors, the disclosure of which is incorporated herein, in its entirety, by reference.

RELATED APPLICATION

This patent application is related to U.S. patent application Ser. No. 13/183,763, filed on even date herewith, entitled, "TREATMENT DECISION ENGINE WITH APPLICABILITY MEASURE," and naming Naresh Ramarajan and Gitika Srivastava as inventors, the disclosure of which is incorporated herein, in its entirety, by reference.

FIELD OF THE INVENTION

The invention generally relates to systems and methods for facilitating medical decisions and, more particularly, the invention relates to generating patient-customized recommendations evaluating treatment options.

BACKGROUND OF THE INVENTION

Traditionally, a single patient to a single physician model is used for medical treatment decisions. Especially when confronted with a complicated disease such as cancer, patients tend to rely on their local physicians for accurate diagnosis, references to specialists, advice on which treatment protocols to adopt and how to proceed. However, the patient and the patient's family are left with several important decisions to make personally. Moreover, their personal abilities to adopt and execute on any of the recommended treatment options may vary. Additionally, in matters where a decision could directly impact the longevity, quality of life, and complete cure for the patient, the decision-making abilities of the patient and family are compromised by the physical stress, anxiety, uncertainty, and lack of confidence that accompany the medical problem. Therefore, reliable information, expert opinion, and trustworthy personalized guidance become necessary to assist patients and their families in making complex medical decisions.

However, it is not trivial to obtain access to and gain an understanding of exhaustive and intensive medical information and expert opinion, especially from world leading medical institutions and repositories of medical literature. Limiting factors include intellectual abilities to understand medical information and opinion, and personal resources such as time, money, and location. Typically, patients and families rely on friends, family members, social networking groups and communities, medical encyclopedias and related websites, as well as relationships with their primary care physicians and specialist doctors for assistance in decision making. Other possibilities include second opinions from medical institutions in metropolitan cities and overseas locations known for their medical research and experience. The Internet, telemedicine and availability of online web services and concierge services to connect patients in different locations with medical experts around the world have opened up additional possibilities for patients to obtain expert opinion at premium costs. For instance, second opinions and pathology/radiology reviews from medical institutions in the United States are becoming a fairly common option pursued by patients in the upper to middle income populations in developing countries.

The efficiency, reliability, accuracy, and effectiveness of such options, however, are questionable. More importantly, none of these services provide a definitive recommendation to follow and the patient's personal preferences, resource limitations, risk tolerances, and to some extent overall medical condition often are not explicitly factored in the medical opinion. A second or third opinion is marginally useful over a primary medical opinion and each additional opinion brings with it added costs and confusions over the final decision, since opinions may be conflicting, contradictory, or unclear. In fields of medicine that are continuously evolving and where research in different parts of the world conclude on widely varying medical paths, second and third opinions can bring with it added complexity and confusion in decision making.

Patients and their families are not the only people with these issues and problems. Others, such as treating physicians and supporting scientists, can face corresponding problems.

SUMMARY OF THE INVENTION

In accordance with one embodiment of the invention, a system and method, for use with a computer system, generate a report to help decide among a plurality of treatment options for a patient with a given medical condition. To that end, the system and method receive patient information related to the patient and the medical condition, and query a treatment option database to generate a plurality of potential treatment options for the medical condition. In a corresponding manner, the system and method also receive preference information indicative of the patient's preference(s) for potential treatment outcomes of the treatment options. The patient's preference(s) are used to produce a preference value. The system and method also analyze indexed study data relating to the plurality of treatment options to produce (e.g., at least in part in a computer process), based on the analysis of the indexed data, a study score for each of the treatment options. Accordingly, for each treatment option, the method and apparatus produce a treatment score as a function of at least the preference value and the study score, thus permitting generation of a report listing the treatment options and a) the treatment scores or b) the information derived from the treatment scores.

The information derived from the treatment scores may be a ranking of the treatment options as a function of the treatment scores for the treatment options. Some embodiments select a recommended treatment option when no other treatment score is within a specified numerical distance of the treatment score for that treatment option. In that case, no single value is used to compute the treatment score that is greater than a threshold based on a second treatment score or the value used to compute the second treatment score. The method and system also may determine if two given treatment scores are within a pre-defined range of closeness to each other, and if so, recalculate the two given treatment scores without using the patient preference information.

In addition, the method and system may compare, at least in part in a computer process, the patient information with at least one studied population to determine the applicability of at least one study to the patient represented by an applicability value. The method and system thus may use the applicability value to weight the treatment scores in favor of treatment options with more applicable study data.

Other embodiments may receive treatment recommendations from a plurality of experts, where the treatment recommendations relate to the plurality of treatment options. Then, these other embodiments may convert, at least in part in a computer process, the treatment recommendations into an expert score for each treatment option, and for each treatment option, determine the treatment score (also) as a function of the expert score. The method and system also may apply an expert weight to the expert score. Among other ways, the expert weight may be calculated using at least one of a ranking of the expert's academic institution, a ranking of the expert's employing institution, the expert's previous success in recommending, the expert's degree of experience, and the relatedness of the expert's qualifications or experiences to treating or working or processing conditions of the patient.

The method and system may store, in an outcome database, treatment decisions by a plurality of patients, together with medical outcomes of the treatments. They may report, to the patient, information derived from the outcome database related to past outcomes. The treatment scores may be determined as a function of the success rate in the outcome database.

Various embodiments also formulate a medical question having patient information, information about the medical condition, and a list of the potential treatment options. The question may be directed to a panel of experts. After receiving response information from the experts about treatment options, the method and apparatus may report the response information to the patient.

Among other things, the indexed study data may be derived at least in part from published studies evaluating the treatment options in a studied population. Moreover, the study score may be a function of at least one of a measure of credibility and the magnitude of effect observed in the study.

Illustrative embodiments of the invention may be implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 3B schematically illustrates an example of a published pamphlet for assisting in determining patient preferences.

DESCRIPTION OF ILLUSTRATIVE EMBODIMENTS

Figure 1:
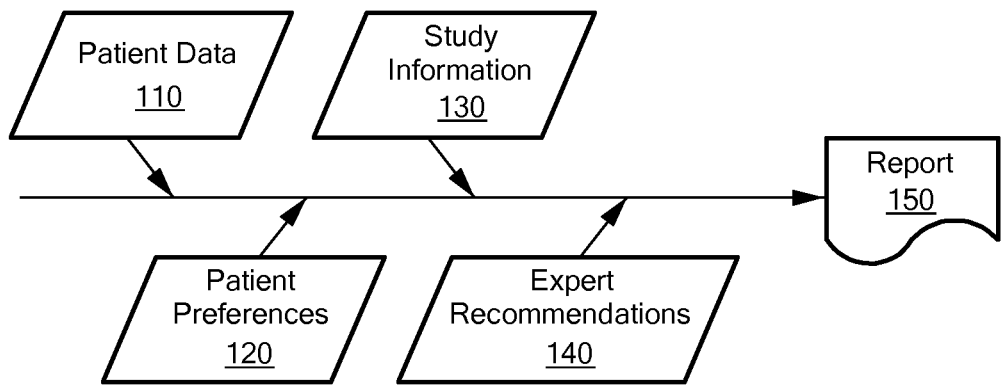
FIG. 1 schematically shows an input and output for a treatment recommendation generation system and process.

Illustrative embodiments of the invention assist people, such as a patient, relative, caregiver, physician, and/or others in the decision-making process, in making complex treatment decisions by enabling access to comprehensive medical literature and opinions from teams of medical experts. The resultant treatment information is presented in a format and language that is easily understood by people who are not medically trained—and in a manner that is consistent with the person's/patient's preferences. In addition, illustrative embodiments can extend beyond people directly involved in a treatment decision. For example, such embodiments can be used in case studies for education purposes, machine learning, for database management/development, and other uses. Discussion of use by a patient and those relating to the decision-making processes thus is for example only and not intended to limit various embodiments.

More particularly, a computerized system generally implements a process, embodied as an algorithm, for aiding a patient or caregiver in making a medical decision (i.e., choosing between multiple potential treatment options). In one embodiment, the system accepts information about the patient, the patient's medical condition, and that specific patient preferences. Next, the system generates a list of treatment options, queries a database of scientific literature ("studies") to determine the potential efficacy of those treatments, and queries experts to receive their treatment recommendations. The various processes may quantify their results to produce scores for the potential treatments. Accordingly, these scores form the basis for a final report to the patient that ranks or otherwise grades each of the treatment options.

To those ends, the system may generate a study score from the studies using, among other things, a measure of the applicability of each study in terms of the degree of correlation between the population studied and the patient. Likewise, the expert recommendations may be converted to an expert score. The study score and the expert score may be weighted using one or more measures of reliability or credibility of the study/experts/authors. Either or both the study and expert scores may be further supplemented using a preference score that represents the value system of the patient. Moreover, the system may further refine the treatment recommendations with outcome score that is based on past medical outcomes of patients that use the system for similar treatments.

Other embodiments may use a subset of the above noted input data to provide a treatment recommendation. For example, the system may deliver treatment recommendations based on the patient preferences and study score only. As another example, the system may deliver treatment recommendations based on the study score and expert score only. Either way may be supplemented by additional data. For instance, embodiments using studies and patient preferences only may supplement with expert opinion.

In general, the steps discussed below may be implemented in a computer system, except where otherwise noted or manual input is needed from the patient or caregiver. Even then, the input is generally obtained by using a computer interface. Details of various embodiments are discussed below.

FIG. 1 schematically shows an input/output scheme for generating a report 150 (or other information) for helping in the treatment decision process. The inputs into the system include some combination of patient data 110, patient preference information 120, study information 130, and expert recommendations 140, as well as prior inputs and outputs of the system. These inputs preferably are entered or converted into the form of quantitative scores (discussed below).

Among other things, the patient data 110 may include descriptive information about the patient, such as age, gender, height, weight, vital statistics, and diagnostic assay data. The patient data 110 also includes the diagnosed medical condition for which the report will be generated. As discussed in greater detail below, the patient preference information 120 is a measure of the desirability of different attributes and outcomes of the various treatment options for the disease. The treatment options may be obtained from a treatment option database having a list of options for the medical condition, while, in a similar manner, the study information 130 may be generated from a database containing information gathered from published or unpublished scientific studies, conference presentations, pharmaceutical data, and the like. The expert recommendations 140 are generated by querying one or more experts with a question about the patient's case. Experts may be chosen or selected by the administrator of the system, and may include any of a wide variety of types of people. For example, among others, the experts may include one or more of people having medical training (e.g., doctors or nurses), researchers, athletes, trainers, former patients, advocates, social workers, or other person as designated by the administrator.

The question may be generated automatically from the patient data, medical condition and corresponding options from the options database. The question is automatically distributed via electronic means, such as email or web or mobile interface, and likewise may be collected automatically for use to automatically generate the report.

Formulating the Medical Question

Figure 2:
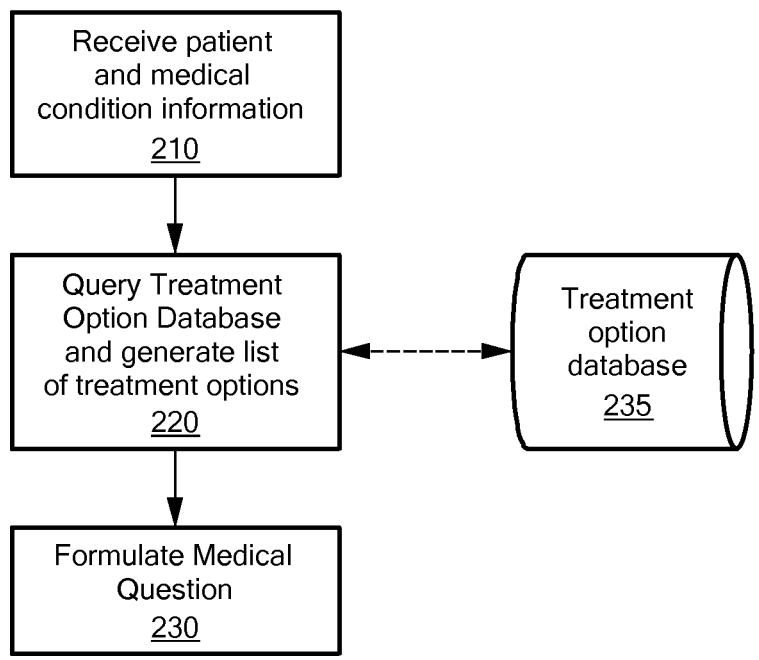
FIG. 2 shows a flow diagram of a process for formulating a medical question.

It is important for the system to generate a relevant and concise medical question for use by experts in forming their treatment recommendations. FIG. 2 generally shows a method for formulating a question for those purposes. In addition to use by the experts, the information in this question also can be leveraged to assist in searching and locating relevant study data, and for determining applicability of certain treatments. Specifically, as noted below, the information in this question can form the basis of both queries to, and supplementing/refining of, the various databases discussed herein.

To those ends, information is received (e.g., from the patient and/or caregiver) about the patient and the medical condition to be treated (step 210). The patient information may include patient records with the patient's age, gender, height, weight, vital statistics, and diagnostic test results. As discussed in more detail below, information about patient preferences and values regarding the acceptability of various treatment outcomes or trade-offs may also be acquired.

Among other things, information collected from the patient may include some or all of the following:
Primary diagnosis for which an assessment of treatment options is sought,
Reports of a history and physical exam as documented by a patient's care provider,
Laboratory results along with reference ranges,
Imaging reports as well as copies of imaging digital or analog imaging, pathology reports as well as digital or analog copies of the pathology slides,
Specimens and staining,
Surgical reports and other invasive and non-invasive procedure reports, both diagnostic and therapeutic in nature,
Discharge summaries, and
Plans of care as made available to the patient.
Demographic data and quality of life data also can be obtained directly from the patient. This list is not intended to be comprehensive, and will develop with time and technology. For example, personalized genomic risk testing is not listed in the sources of information above (except referred to broadly as laboratory testing), but may be included as its availability matures.

After collecting the information from the patient, the system abstracts relevant data from the record for entry into a secure database in a standardized format. Data that is considered relevant may include demographic data of the patient (e.g., age, gender, ethnicity, race, socio-economic scale, education level, home location, and the like), medical data of the patient (primary diagnosis, other medical problems, substance exposures, prior treatments etc.), functional data on the patient (quality of life scores, Activities of Daily Living (ADL) scores etc.), and data on the sources of information (lab names, hospitals, primary physicians, city/country etc.).

To develop a list of potential treatment options, the medical condition information is entered into a query of a treatment option database 235 (step 220). The treatment option database may be formed in any number of manners. For example, past treatment experience, experts, clinical guidelines or study data may delineate potential treatments for specific illnesses and store that information in the treatment database. The query thus returns potential treatment options (discussed below). The patient information, medical condition and treatment options are then summarized and translated into medical language (i.e., "medical-speak") for subsequent use (the medical question, step 230).

This process can be automated or completed manually by a team of those trained in the process.

Example 1. Patient speak—"I've recently been diagnosed with an aggressive form of Leukemia and have finished induction chemotherapy. My doctors are asking me to consider a bone marrow transplant. I've heard this treatment has a high risk of death. What should I do?"

Example 2. Patient speak—"I was diagnosed with prostate cancer two years ago. My surgery wasn't completely successful, but my PSA is negative. What should I do?"

Example 3. Patient speak—"My mother has metastatic breast cancer, and it has now spread to her brain. Her doctors want her to have whole brain radiation, but I'm not sure. What should I do?"

Translated in medical speak, the medically relevant question has several important parts:

Description of the patient. This section of the medical question defines the medical characteristics of interest to the evidence and experts, and includes the variables usually used in research and clinical practice that were collected in step 1, including demographics, medical data and functional data.

Example 1. The Patient in medical speak:
In a 25 year old, otherwise healthy, currently employed, Hispanic male with diagnosed FLT3 positive Acute Myeloid Leukemia, with a white blood cell count of 250,000, completed induction therapy with Daunarubicin and Cytarabine with successful remission—

Example 2: The Patient in medical speak:
In a 78 year old Caucasian gentleman with a past medical history of controlled diabetes, hypertension, hyperlipidemia, atrial fibrillation and history of an embolic stroke with mild residual left sided motor deficits, currently living independently with his spouse, diagnosed with Gleason grade 9 locally advanced prostate adenocarcinoma s/p radical prostatectomy with extracapsular invasion 15 months prior, with a PSA<0.1—

Example 3: The Patient in medical speak:
In a 45 year old African American lady with HIV related dementia, living in a nursing home, with stage III Her2-Neu negative, ER negative, PR negative ductal breast adenocarcinoma s/p mastectomy and 4 cycles of induction Doxorubicin & Cyclophosphamide therapy two years ago, with a new right frontal lobe 2 cm metastatic lesion—

Description of potential outcomes. The formulated question may also contain a description of the potential outcomes. The treatment options are to be evaluated (in later steps) in connection with these possible outcomes. For example, for a serious condition, the outcomes may include all-cause mortality (total mortality), cause-specific mortality, and/or quality of life. For certain diagnoses, an outcome of disease-free survival or progression-free survival may also be entertained.

Description of the options. The question includes a list of treatment options to be evaluated. The treatment options include interventions as well as controls by which they are compared. Accordingly, there should be at least two options for each question. The second option may be the option to do nothing therapeutically until further problems arise ("expectant management").

These options are generated based on an understanding of the patient's problem in their terms, their medical information, the usual standards of treatment for a disease, other treatments available in the literature and reviews, and, if needed, in consultation with experts.

Example 1. Leukemia
    A) Autologous Bone marrow transplant
    B) Allogeneic Bone marrow transplant
    C) 6 cycles of consolidation therapy with Doxyrubicin, Cyclophosphamide
    D) 6 cycles of consolidation therapy with abxicimab Example 2. Prostate Cancer
    A) X-ray beam radiation therapy
    B) Proton beam radiation therapy
    C) Hormonal therapy with triple androgen blockade
    D) Radiation therapy plus hormone therapy
    E) Expectant management with close monitoring Example 3. Breast Cancer
    A) Whole brain radiation, with focal stereotactic radiation to mass
    B) Focal surgical resection of mass followed by whole brain therapy
    C) Focal surgical resection of mass with chemotherapy
    D) Focal surgical resection of mass, followed by WBR, followed by chemotherapy
    E) Whole brain radiation alone
    F) Expectant management Example 4: A translation of a patient's problem from patient speak to medical speak using the medical condition and treatment options of example 2:

Patient question: I was diagnosed with prostate cancer two years ago. My surgery wasn't completely successful, but my PSA is negative. What should I do?

Figure 3A:
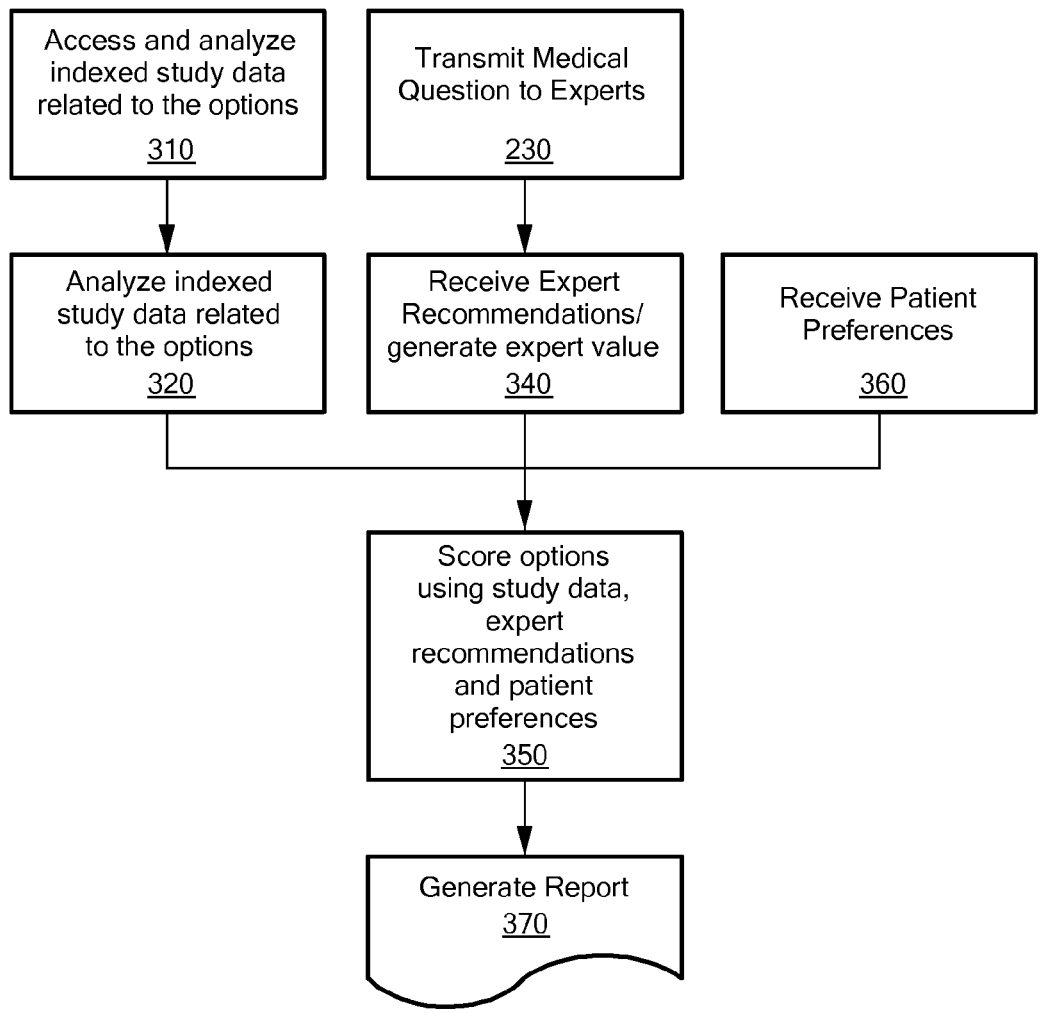
FIG. 3A shows a flow diagram of a process for generating a treatment recommendation report in accordance with the embodiment of FIG. 1.

Medical Question: In a 78 year old Caucasian gentleman with a past medical history of controlled diabetes, hypertension, hyperlipidemia, atrial fibrillation and history of an embolic stroke with mild residual left sided motor deficits, currently living independently with his spouse, diagnosed with Gleason grade 9 locally advanced prostate adenocarcinoma s/p radical prostatectomy with extracapsular invasion 15 months prior, with a PSA<0.1—
(Patient Information)
With respect to overall morbidity and mortality—(outcome)
Which is the next best step in management—(interventions and controls)
    A) X-ray beam radiation therapy
    B) Proton beam radiation therapy
    C) Hormonal therapy with triple androgen blockade
    D) Radiation therapy plus hormone therapy
    E) Expectant management with close monitoring Quantitative Representation of Information Sources FIG. 3A shows a system for generating quantitative descriptors to evaluate the desirability of the various treatment options for the particular patient. By parameterizing and quantifying the descriptors, the obtained values can be easily used to recommend decisions, and in machine learning algorithms. To those ends, indexed study data (e.g., from published scholarly articles for clinical trials) is accessed (step 310) and analyzed relative to the treatment options (step 320). For example, the system can enter data from the question discussed above into a search template that searches the indexed data. Other data also can serve as input into the search template. Search data can include, among other things, codes or keywords relating to the disease, treatment options, age of patient, effect size, or grade of the study/paper. After analysis of the study data, the system provides a quantitative recommendation for the best treatment, the second best treatment, etc . . . based solely on the study data. At the same time, or at some other time, the question is presented to experts (step 230) and, based on their evaluation of the options; the system generates expert values for the options (step 340). The system also queries and receives patient preference values for the potential outcomes of the options (step 360). All of these values are combined to generate combined scores and/or rankings for the treatment options, and a final report that includes (or is derived from) the scores or rankings (step 370).

In some embodiments, merely using two of these options still can deliver a treatment ranking. For example, only the study data and patient preferences can be used to provide a treatment recommendation.

Expert Query

To obtain expert feedback, the medical question is transmitted to a group of qualified experts for evaluation—i.e., to solicit their opinions as to the most appropriate treatment(s). Among other ways, the question may be transmitted by email and may include a link to a web-interface for entering their recommendations, or by mobile or cellular communication with an interface for entering their recommendation. In one embodiment, between ten and fifteen experts are surveyed. Of course, the number could be more or less depending on factors, such as need and cost. Each expert assigns one or more scores to the desirability of each treatment option.

In various embodiments, the expert recommendations are weighted by a factor derived from information correlated with the credibility and characteristics of each expert. Such indicia may include, among other things, a ranking of the expert's academic institution, the institution where fellowships/training was received, institute of the expert's current professional affiliation, years of experience, education, certifications/credentials, past performance, and the like. In the case of a medical practitioner, information such as the number of patients processed, direct or indirect relation/fit with the type of disease and treatment option, and self-declared fits, and the like may also be considered. For example, an expert rank may be derived from: a reputation score of the institution with which the expert is affiliated, an experience score based on years of practice, and an expertise score based on the specific diagnoses in the question and its applicability to the practice of the expert consulted. Alternatively, the expert rank can simply be manually/statistically assigned based on one or more factors.

For example, the reputation score may be determined using published rankings for institutions (e.g., from US News and World Report), from a survey of experts within the system of various embodiments, or based on outcomes of patient's treated according to the expert's recommendation. The outcomes may be stored in an outcome database from which the system can correlate expert's individual decisions with desired outcomes and rank reputation using that information.

In the case of a medical practitioner or physician, experience score can be based on the number of years in clinical practice after completing residency or fellowship training in the area of expertise. For example, for a neurologist with a fellowship in movement disorders, the relevant training of commenting on a general neurology case would be post-residency experience and, if on a movement disorders case, would be post-fellowship experience.

The expertise score can be an estimate of how closely matched the expertise of the expert is to the medical condition of the patient. For example, all hematology/oncology fellowship trained physicians are able to treat blood cancers, though some may have greater a greater expertise score because they have self-defined expertise in lymphoma and others in leukemia. This score can be obtained through a self-definition of expertise by the consultants, and/or by assessment of their research interests, published papers and patient population.

Combining these elements in a normalized, weighted fashion produces an expert rank. Each expert selects an option, and their options are calculated together with the rank to produce a final expert score for each option.

Among other ways, the expert score may can be expressed as:

Expert score for option 1=normalization function (Expert rank$^1$*option 1+Expert rank2*option 1+ . . . )

Expert rank=normalization function (reputation score+experience score+expertise score)

In alternative embodiments, the expert recommendations are not weighted by any factors, such as reputation, expertise, etc . . . .

Literature Analysis

The study data preferably is created, curated and maintained in an indexed database. Among other ways, the study data may be keyword indexed for easy word searching (i.e., all words are indexed for search). In addition, the study data also may be indexed based on a number of other factors, such as disease type, treatment options, results of the treatment, people in the study, and other relevant study data. Accordingly, unlike databases with studies in their native form (e.g., databases having copies of articles and studies in whole or in relevant part), the indexed database has data drawn directly from articles/studies and indexed in an easy to analyze format.

The system may index the data to create this database, which may be presented a plurality of forms, such as a spreadsheet, in a number of different ways. For example, the data in the indexed database may be manually drawn from the articles for entry in the indexed database. Alternatively, or in addition, the data may be automatically drawn from the articles through some computerized algorithm configured to 1) locate relevant data (e.g., tables of results, information about the study authors, and the like) and 2) enter such data in to the study database. Some of the relevant data may include bibliographic information relating to the study or article, how the disease is defined based on the study participants, treatment criteria, and the patent population demographic information. Examples of such information include:

Bibliographic: publication identifier, title, authors, journal title, years of publication, volume/issue number, pages, online link, and methodology.

Disease definition: age ranges, menopausal status, mass dimensions, histology, molecular types, physiological factors Treatment criteria: treatment timing, surgery, radiation, chemotherapy, Patient Population Demography: age ranges, race, gender, number of lymph nodes positive, tumor size, Curation of the study database may include discarding known fraudulent or non-credible studies. Alternately, such studies may be modified by a low or zero weighting factor. As noted above, using relevant information such as the medical condition and possible treatment options, the system queries the database to arrive at an evidence score. Furthermore, an applicability score may be used to account for differences between the studies populations and the patient information.

The system thus queries the medical literature database for evidence specific to the question and, based on this query, assigns a quantitative study score for each option. The study score is a numerical combination of variables that reflects one or more of the internal or external validity of studies, and with the effect size predicted from the intervention that is being studied.

Internal validity of the data can be assessed by grading the evidence. There are numerous ways to grade, including the published metrics that follow. For example, grading may be based on methodology, effect, and patient applicability. Grading could be based on a relative scale with respect to other treatment options. Two different ways to grade the evidence are described below. Other ways are published online, including the emerging consensus on using the GRADE standards.

From the United States Preventive Services Task Force Levels of Evidence:

Level I: Evidence obtained from at least one properly designed randomized controlled trial.

Level II-1: Evidence obtained from well-designed controlled trials without randomization.

Level II-2: Evidence obtained from well-designed cohort or case-control analytic studies, preferably from more than one center or research group.

Level II-3: Evidence obtained from multiple time series with or without the intervention. Dramatic results in uncontrolled trials might also be regarded as this type of evidence.

Level III: Opinions of respected authorities, based on clinical experience, descriptive studies, or reports of expert committees.

From the National Cancer Institute Levels of Evidence for Adult and Pediatric Cancer Treatment Studies:

Study Design (in descending order of strength)
1. Randomized controlled clinical trials.
   1. Double-blinded.
   2. Nonblinded treatment delivery.
   3. Meta-analyses of Randomized Controlled Trials
2. Nonrandomized controlled clinical trials.
3. Case series.
   1. Population-based, consecutive series.
   2. Consecutive cases (not population-based).
   3. Nonconsecutive cases.

External Validity of the evidence is the applicability of the clinical evidence to the patient or clinical context (e.g., the medical question). More particularly, many studies are performed on a sample population that is not relevant to the population being tested. For example, the celebrated and much cited Framingham cardiac risk factor study was a longitudinal cohort study (Level II in the parlance noted above) that primarily included suburban, Caucasian men and women in its subject population. Yet, it is widely applied to predict risk in young, urban, Armenian immigrants who may be exposed to cocaine or other risk factors not prevalent in the Framingham population. Hence, though the Framingham study may have good internal validity, its external validity to the particular patient it is being applied to may be lacking. Accordingly, for more refined results, it is desirable that the evidence be applicable to the patient.

The external validity of the study to the particular patient can be quantified by assigning an applicability score. The system can calculate the applicability score by forming an index defined as a ratio having a numerator and a denominator. For example, to determine the numerator, the patient characteristics of the key studies that answer the clinical disease-specific question are pooled together, focusing on both percentages and number of subjects enrolled across all reported variables that match the patient's information. The denominator of the index includes the number of categories analyzed by the studies. In another embodiment, the numerator is the number of matches for each variable, and the denominator is the total number of variables described in the study. Factors that are new or relevant but not included in the patient characteristics of the published data will reduce the applicability index by a predefined amount.

For example, the discussion below illustrates the index weighting using a landmark trial showing the efficacy of Herceptin in Her2/Neu positive breast cancer in addition to systemic chemotherapy: Romond E H, Perez E A, et al. Trastuzumab Plus Chemotherapy for Operable HER2-Positive Breast Cancer. *NEJM, Vol.* 353. No. 16, pp. 1673-1684.

In a 45 year old African American lady with HIV related dementia, living in a nursing home and helped with her ADLs, with stage III Her2-Neu positive, ER negative, PR negative ductal breast adenocarcinoma s/p mastectomy and 4 cycles of induction Doxorubicin & Cyclophosphamide therapy—
Table 1 (Baseline Characteristics) in the paper cited above gives us the following information that is relevant to our example patient:
Trial site (North America & Europe): 71.3% (1208)
Race (Black): 0.7% (12)
Age 35-49: 44.3% (751)
Pre-menopausal: 16.1% (272)
1-3 positive nodes: 28.5% (482)
Tumor Size (2-5 cm): 44.6% (756)
ER neg, PR neg: 47.1% (798)
(many other characteristics in table 1 are ignored for now, for brevity's sake)
Applicability index for this trial to this patient would be, for example Numerator=4279, Denominator=7 categories, Index=611

In general, the index will be higher if: 1) the trial is large, 2) more characteristics of the patient are represented in the trial, and 3) the percentage of the trial subjects fitting the patient characteristics are larger.
In one embodiment, the formula for the index can be expressed as follows:

$$\text{Applicability index} = k \cdot \Sigma h 1(n \text{ per matching category}/\# \text{ of categories})_{study\ 1} + \ldots$$

Other factors that might be included in this equation include the percentage of subjects in trial in the matching category, and strength of endpoints. The constants k and h are added in to represent weights and constants needed to normalize the data.

The effect size of the study evidence is calculated using a combination of the reported endpoints and their strength. The strength of the endpoints can be judged as delineated in algorithms below, or in similar ways and weighted accordingly. This can be multiplied by the absolute effect size found in a trial, and can be compared option by option.
From the National Cancer Institute Levels of Evidence for Adult and Pediatric Center Treatment Studies, Strength of Endpoints (in descending order of strength)
  1. Total mortality (or overall survival from a defined time).
  2. Cause-specific mortality (or cause-specific mortality from a defined time).
  3. Carefully assessed quality of life.
  4. Indirect surrogates.
    1. Event-free survival.
    2. Disease-free survival.
    3. Progression-free survival.
    4. Tumor response rate.

For example, in the same trial cited above, the absolute effect for disease free survival events at 2 years was 8.4% more in the Herceptin group compared to the chemotherapy and surgery only group, and Progression free survival was 7.8% more as well. All cause mortality was not significantly different between the two groups at 2 years.

Accordingly, the effect size score for an option of Herceptin plus chemotherapy can be calculated using a combination of the strength of the endpoint in the trial with the effect seen itself. This can be averaged and weighted over multiple trials selected as part of the evidence to be considered for the option.

Overall, the evidence based formula for each option can be expressed as:

$$\text{Evidence score} = \text{normalization function (weight*grade of evidence + weight*applicability index + weight*effect size)}$$

Patient Preferences/Risk Tolerance

The system illustratively queries the patient with a patient preference tool specific to the question, and assesses a patient preference score for each option. The patient preference score may be based on, for example, the patient's risk tolerance, lifestyle values, and cost considerations. In addition, the patient preference score may be computed at least in part using a risk tolerance score (RTS). Specifically, the RTS assesses how the patient judges and prioritizes the inherent risks and benefits of each of the options. The RTS is a score/value designed to understand the general risk tolerance of the patient to each option. The risks can be expressed as letters, numbers, percentages, probabilities, color scales, temperatures or any other means of determining grading and uniform space between progression of grades.

Before and/or while gathering the patient preferences, the system may present information about the disease, information about the prognosis, pros/cons, risks, and other relevant data. This information may be derived from any number of sources, such as the studies/literature, reliable web sites, previous patient data from this system or other systems, and experts. Rather than using exact probabilities, the system may measure and present this information along a grading spectrum, in other forms. For example, the system may present this information as some easy to understand visual indicia, such as pie charts, exclamation points, happy faces, gold coins, or bombs. As another means for explaining the information, the system may compare risks to other events to which a patient may relate, such as comparing the risk to that of being struck by lightening, being in a plane crash, or stepping in a puddle on a rainy day.

The patient preference tool (e.g., a webpage or applet) may query the patient about preferences, and direct those preferences into the computation modules of the system. An RTS tool, which may be part of the patient preference tool, may measure risk tolerance. In one embodiment, the risk/benefit categories and grades may be plotted on a Y axis of a RTS tool. The patient's acceptability score, also expressed as a scale with uniform distance between grades on the scale, may form the X axis. The categories of patient acceptability may be expressed qualitatively as used in Likert scales, or quantitatively in terms of probabilities or percentages of acceptability.

Each item in the risk/benefit categories may be predetermined and defined for the patient in the context of their illness. For example, use of the words "major side effects" may mean highly morbid or fatal side effects of the particular chemotherapeutic agent that are known, and will have a different specific meaning for each option that can be given to the patient as desired. In another example, "Quality of life" as defined as the ability to perform activities of daily living to compare medical treatments is different from a more broadly understood but less quantifiable version of its meaning including "happiness", "contentment" and the like. The RTS assessment may include redundant questions asked in multiple different ways to assess each option thoroughly.

The RTS tool can be administered to the patient with the risk/benefit categories on the Y axis filled in for their diagnosis and each treatment option, and the acceptability score can be entered by the patient for each category on each option. This allows the system to compute an overall RTS for each option, and then to comparatively assess, which option is better desired by the patient in terms of risks and benefits. Below is an illustrative blank scale for one embodiment:

Option A: X type of therapy

| Option A | Intolerable | Tolerable | Desirable |
|---|---|---|---|
| Low chance of major side effects | | | |
| Low chance of cure | | | |
| High - quality of life | | | |

Following through with example 2 might be helpful to illustrate the RTS. In the example below, each outcome is granted an equal weight of 1 to make calculations simpler.

RTS for Example 2, Prostate Cancer. Option A: X-ray beam radiation therapy

| XRT | Will not tolerate (1) | Tolerable (2) | Acceptable (3) | Preferable (4) | Optimal (5) |
|---|---|---|---|---|---|
| 30% risk of major side-effect | | 2 | | | |
| 30% risk of treatment failure | | | 3 | | |
| 50% chance of cure | | | | 4 | |
| 50% chance of increased QALY | | | 3 | | |
| 50% Cost-effective treatment | | | 3 | | |

Risk tolerance score for Option A is 15/25=60%

RTS for Example 2, Prostate Cancer, Option D Expectant Management.

In this example, the chance of cure is weighted higher (1.5) for demonstration

| Expectant Management | Will not tolerate (1) | Tolerable (2) | Acceptable (3) | Preferable (4) | Optimal (5) |
|---|---|---|---|---|---|
| 0% risk of major SE | | | | | 5 |
| 50% risk of treatment failure | | 2 | | | |
| 20% chance of cure | | 2 | | | |
| 80% chance of increased QALY | | | | | 5 |
| 100% Cost-effective treatment | | | 3 | | |

Risk Tolerance score for Option D, expectant management is 17/25=68%

In other embodiments, the RTS includes as Patient Preference Tool (PPT). Specifically, in such embodiments, the PPT is a preference and value elicitation tool that uses scientifically validated techniques for decision aids in order to quantitatively determine the contribution of a patient's preference for a treatment option towards the final treatment choice.

In states of clinical uncertainty or equipoise, patient preference typically is a determining factor in treatment choice. Several studies, including a Cochrane Review of Randomized Controlled Trials have stated that "decision aids improve people's knowledge of the options, create accurate risk perceptions of their benefits and harms, reduce difficulty with decision making, and increase participation in the process. They may have a role in preventing use of options that informed patients don't value without adversely affecting health outcomes." (O'Connor 2009, Cochrane Library).

Several statistically validated methods for preference elicitation have been described and may be used, including:

1. Adaptive Conjoint Analysis (ACA)
2. Willingness To Pay for Quality Adjusted Life Years (WTP for QALY)
3. Standard Gamble & Treatment Trade Off Methods
4. Decision Boards, Leaning Scales and Rating Scales Preferred embodiments may implement Adaptive Conjoint Analysis (ACA) as the underlying method of choice, although some embodiments may combine presentation methods from other models as well. As known by those in the art, ACA elicits preferences regarding distinct dimensions associated with treatment options. The exercise primarily asks participants to rate combinations of treatment dimensions that involve trade-offs (typically because a gain in one dimension is related to loss in another). The trade-offs are similar to the way individuals make decisions in real life. As ACA asks about valuations of underlying dimensions related to outcomes, it provides insight into the basis of preferences. Results therefore extend beyond particular medical conditions.

Information Presented:

Information is presented in text and graphics regarding the disease and the treatment options, from nationally cancer institute statistics, and reputable published randomized controlled trials, and will be referenced appropriately.

This material will be developed with particular focus to educational level, socio-economic status, and available, culturally appropriate materials.

As an example, FIG. 3B shows a published pre-existing information pamphlet for Mastectomy vs. Lumpectomy+Radiation for early stage breast cancer.

Dimensions on Survey:

Dimensions of care that appear with regard to decision making may include:

1. Overall Survival
2. Quality of Life
3. Side Effects
4. Total Cost

Depending on the particular situation (e.g., early stage cancer, etc.), additional dimensions, such as Local Control or Disease-Free Survival, may be assessed as well.

Sample Questions Design (Adaptive Conjoint Analysis Methodology):

Stage 1—Individual Factors

| Mastectomy | Lumpectomy + Radiation |
|---|---|
| Loss of Affected Breast | Change in Appearance of Affected Breast |

"All other things being equal, how important is this difference to you?"

| 1 | 2 | 3 | 4 | 5 |
|---|---|---|---|---|
| Not Important | Somewhat Important | Important | Very Important | Extremely Important |

Stage 2—Combination Factors and Trade-Offs

| Mastectomy | Lumpectomy + Radiation |
|---|---|
| Loss of Affected Breast | Change in Appearance of Affected Breast |
| Total Cost = x Rs. | Total Cost = 3x Rs. |

| Strongly Prefer Left | Somewhat Prefer Left | Neutral | Strongly Prefer Right | Somewhat Prefer Right |
|---|---|---|---|---|
| 1 | 2 | 3 | 4 | 5 |

Alternate Design (Treatment Trade Off Methodology):

Option 1: Mastectomy

| Mastectomy | Not Desired (1) | Somewhat Desired (2) | Desired (3) | Very Desired (4) | Extremely Desired (5) |
|---|---|---|---|---|---|
| 35-60% 20 year survival | | | | 4 | |
| 2-5% local recurrence in 20 years | | | | 4 | |
| 100% chance of sig cosmetic difference w/o use of prosthesis or recon | | 2 | | | |
| Cost of X. Rs for treatment | | | | | 5 |

Option 2: Lumpectomy with Radiation

| Lumpectomy + XRT | Not Desired (1) | Somewhat Desired (2) | Desired (3) | Very Desired (4) | Extremely Desired (5) |
|---|---|---|---|---|---|
| 35-60% 20 year survival | | | | 4 | |
| 5-10% local recurrence in 20 years | | | 3 | | |
| 20% chance of sig cosmetic difference w/o use of prosthesis or recon | | | | 4 | |
| Cost of 3X. Rs for treatment | | 2 | | | |

The RTS can be expressed as a function of pre-defined weighted quantified outcomes across grades of acceptability to the patient:

$$RTS = \text{normalization function } \Sigma(\text{weight of outcome } y1, 2, 3 \ldots) * (\text{grade } x1, 2, 3 \ldots)$$

Outcome Database and Machine Learning

The system may store, in an "outcome database" (noted above), the patient information and results of the various queries and analyses mentioned above, using a machine-learning engine. Specifically, by tracking actual decisions about treatment options, and the medical outcomes of those treatment options (short term, medium term, and long term), the system enables additional information for making informed decisions. In addition, statistics about other patient's choices and results may be included in the report 360. Alternately, or in addition, the outcome information may be included as a separate score used to rank the treatment options.

To use this outcome database, a machine learning algorithm, of a machine learning module/engine, may execute the following steps:

1. Query the outcome database using the patient's information and the question to find strength and number of matches in the database and, consequently, calculate a confidence score for the question. The confidence score indicates the degree of similarity between the patient's information being queried to that of the population of patient's information stored in the outcome database. This may be accessed through any number of factors, such as similarities in demographic data and/or medical specific data. For example, if the age in the query is 45, then the system may consider the population of patients in the 43 to 47 range as a proxy for understanding whether the outcomes that they faced may be applicable to the patient in question. In this case, the predefined minimum is the confidence interval of +/−2 years. So, if there is no patient in the population in the ages of 43 and 47, then the confidence score is zero and system may or may not use the outcome database as a source. The confidence score may be expressed in any predefined manner. For example, if in the above age example, if ten studies were reviewed and only two were within the confidence interval, then the confidence score of that factor may be 20 percent.

Even if the confidence score of a single criteria is zero or very low, such as in the age example above, the system still may consider other factors to calculate an overall confidence score. Among other things, those other factors may include disease, weight, geography, gender, and ethnicity. The system thus determines which factors must match and to what confidence interval, and whether all factors, or some of the factors, must match. This determination may be pre-programmed, or determined based upon a pre-defined algorithm. The final confidence score thus can be a function of all the confidence score of all the factors based on some pre-defined formula or method. Alternatively, or in addition, the confidence score can have some other requirements, such as if any of the factors has a confidence score of below or above a certain amount, then the final confidence score is a pre-set amount (e.g., zero for a low score, or 100 for a high score).

Figure 4:
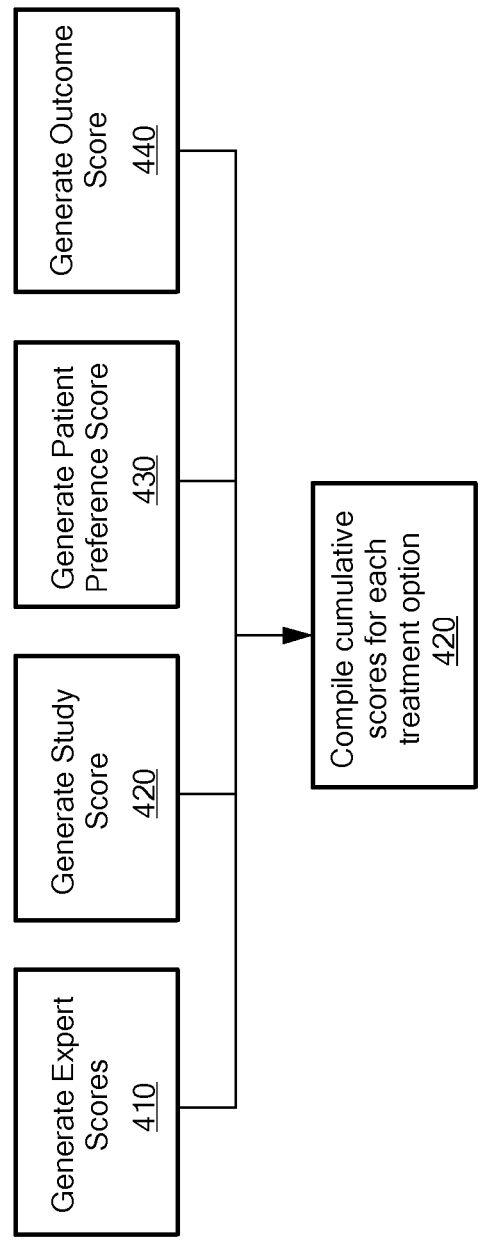
FIG. 4 shows a flow diagram of a process for generating combined scores for use in generating the treatment recommendation report.

2. If the confidence score is less than a pre-defined minimum, return no answer and the decision making process of FIG. 4 is followed (explained below)

3. If the confidence score exceeds a pre-defined high:
    a. Stratify the options by outcome and calculate a total outcome score for each option, and
    b. Combine the patient's risk tolerance score for each option with the total outcome score for each option and choose the option with the highest score (the "decision").

4. If the confidence score is intermediate (i.e., between the pre-defined high and the pre-defined low),
    a. Proceed with an outcome based decision as in step (3)
    b. Confirm the decision with prior expert scores and study scores recorded in the outcome database (non-RTS score).
    c. In the case of agreement between with the outcome based decision (4a) and the prior expert scores and study scores (4b), the decision is finalized and released.
    d. In the case of disagreement between 4a and 4b, use the decision-making process of FIG. 4.

Interaction of the Machine Learning and Decision Making Algorithms

1. Machine learning module consistently assesses the recommendations of the decision making algorithm based on outcomes collected, 2. Differing weights are assigned to the decision making algorithm's variables to maximize prediction of outcomes, 3. New variables may be added or subtracted to the decision making algorithm's equations based on outcomes found by the machine learning module, 4. The decision making algorithm's weights and variables may be adjusted in a disease-specific manner based on the machine learning module's analysis of the outcomes and their relation to the individual variables in the decision making algorithm, 5. If the machine learning module's decision (outcome based) and decision making module's decision (evidence and expert based) are persistently different once high confidence is achieved despite tuning of weights, manual scientific review of the outcome selection, evidence gathering process and expert opinion will be prompted. This is an opportunity for breakthroughs in treatment strategies through the learning from experience and routine care.

Interaction of the Machine Learning Module and Outcome Database

1. New variables may be added into the outcome database and assessed by the machine learning module for inclusion into the algorithms for the decision making algorithm and/or to assess for a match and confidence score with new patient records. For example, weight may be a variable in determining the effectiveness of chemotherapy doses. Or, to match a patient with the patient population in the outcome database, the system may also consider co-morbidities, such as hypertension, also as a match (even though the system may be evaluating cancer treatments). So, if the patients in the outcome database have the same type of cancer and they have hypertension, (like the patient in question), then the system may consider their outcomes to be a proxy or factor in determining the recommended treatment option for the patient in question.

2. The fidelity of the data in the outcome database can be continuously improved. Initially, data may be considered of medium fidelity as sources are known but not verified. Over time, only high fidelity, trusted and verified source data may be included into the database. Although this process of ensuring fidelity of data is expected to be internal to the outcome database, at some point it may be incorporated into the confidence scoring system employed by the machine learning module.

3. The outcome database itself becomes an asset for review, research and learning by experience.

The algorithms described above help in choosing treatment strategies for complex medical problems. However, the basic concept in an abstract form can be stated as below.

Accordingly, as noted, many of the illustrative algorithms above reduce complex problems into limited discrete options that are evaluated numerically based on a combination of two or more of the following: 1) patient preference, 2) standardized quality metrics, 3) studies/evidence, and 4) expert judgment. These parameters help make an informed treatment decision. This decision can then be tracked, and the algorithms improved and supplemented by using a database to monitor outcomes and adjust the algorithm based on desired outcomes. For example, some methods may choose the best techniques for preventing disease based on patient preference, evidence, and expert recommendations.

Ranking of Treatment Options

FIG. 4 shows a process for recommending a medical decision. As described above, for each treatment option, the system generates one or more of an expert score (step 410), a study score (step 420), a preference score (step 430), and optionally (when available) an outcome score based on the results from previous medical cases that the system assessed (step 440). The system then compiles these scores into an aggregate score for each treatment. The system may then present the result in some form, such as a report listing the treatments and their rankings or scores. Alternatively, the system may choose or deliver the option with a predefined type of score (the "decision"). In other words, the system may choose or deliver a treatment based upon a score having one or more specific attributes. For example, that score may be the treatment with a) the highest score, b) a mean, median, or lowest score, c) an even number, or d) a specific coding or encoding criteria (e.g., a score ending in a letter where scores are encoded in alphanumeric formats). As yet another example, that score may be one that differs from the majority, or one that is different in some way from all other scores. Groups of treatments also may be recommended based on other scoring formats/decisions. Accordingly, discussion of delivering the highest treatment score is by example only.

In illustrative embodiments, the generated treatment options each have aggregate scores with three distinct parts that can be combined together. Combination of the parts may include statistical normalization to compare and add values along a common scale.

In one embodiment, for a treatment option to receive the highest common score, two conditions must be satisfied: 1) No other common score must be within a pre-defined range of closeness to the decision, and 2) no one component of the decision score must be so high as to be greater than the second highest common score. These provisions prevent decisions made on very narrow margins as well as decisions that are unduly swayed by certain experts or strong preferences of the patient.

In cases of common scores within a pre-defined range of closeness to each other, the cumulative scores can be recalculated using just the study score and expert scores. If a decision of which score is most appropriate can now be made, then it will be presented as such, and state why the patient preferences were removed from the equation to facilitate decision making. Alternatively, if the sum of the study/evidence and expertise scores are within a pre-defined range, and the cumulative score is making a narrow decision, then the decision can be made using the preference score, with disclosure and the caveat that the preference score is the deciding factor in the score.

For example

Case 1:

Option A=Preference score 20+Evidence score 40+Expert score 40=Total Combined Score=100

Option B=Preference score 40+Evidence score 30+Expert score 30=Total Combined Score=100

Pre-defined limit of equality=10 points

In this case, the preference score equalizes the difference between Option A and Option B. The decision is made as Option A (80 non-preference score points) and is explained as to why the preference score is calculated by excluding it from the final score in order to permit a decision based on the evidence and expertise score.

Case 2:

Option A=RTS 32+Evidence score 35+Expert score 33=Total Combined score=100

Option B=RTS 29+Evidence score 37+Expert score 34=Total Combined score=100

Pre-defined limit of equality=10 points

In this case, all three components are within a pre-defined range of equality. However, the preference score is allowed to decide the decision for Option A. Specifically, Option A is decided in this case because there is no significant difference between the evidence and expert scores for the options, and the preference score prefers A slightly over B.

In one embodiment, in cases of conflict, rules such as the following may be used: the evidence score>>expert score>>preference score. However, similar evidence and expert scores within the pre-defined limit of equality will most often be considered equal, but the close scores on the preference score can still serve as tie breakers.

The Report

The system generates a report 150 summarizing at least one of the following: the medical information, the diagnosis, information about the diagnosis, the options, the patients risk tolerance, the medical literature on the options, the expert opinions on the options, treatment ranking, and the decision to be returned to the patient. Alternatively, the report may include a much smaller amount of information, such as simply the top scoring treatment option (information derived from the treatment scores). In any case, the report can take on the form of any conventional medium, such as printed on paper, on a display monitor, or simply as data for storage or transmission to another device.

This reporting process requires a re-translation of the medical terminologies in the report into an easily understandable, patient-centered and patient-specific report. To facilitate patient understanding, the report illustratively contains the components of the decision making process, along with information about the diagnosis, summaries of evidence, and expert opinions.

The report generation module uses the information sources discussed above and translates 1) the qualitative characteristic of the evidence based medical literature and 2) medical opinions from the panel of experts into quantitative representations that can be manipulated and computed by the system's decision making and machine learning modules. For example, the nature and learning of each of the components of evidence based literature that is factored into system's decision making is reduced to a score that represents its relevance to the patient and the decision recommendation. Similarly, each of the opinions or options that the experts select can be reduced to a score with associated weights that can be combined to compute a consensus score representing the opinion valued by the most relevant and experienced experts in the field. The recommendations and/or outcomes for prior patients are also represented numerically and stored in the outcome database. These scores are then factored into the decision making for subsequent patients by easily combining them with new information scores.

Various embodiments of the present invention may be embodied in many different forms, including, but in no way limited to, computer program logic for use with a processor (e.g., a microprocessor, micro controller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) in a tangible storage medium, such as a semiconductor memory device (e.g., a RAM, ROM, PROM, EEPROM, or Flash-Programmable memory), a magnetic memory device (e.g., a diskette or fixed disk), an optical memory device (e.g., a CD-ROM), a PC card (e.g., PCMCIA card), or other memory device. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or temporarily in a tangible storage medium, such as a semiconductor memory device (e.g., a RAM, ROM, PROM, EEPROM, or Flash-Programmable memory), a magnetic memory device (e.g., a diskette or fixed disk), an optical memory device (e.g., a CD-ROM), or other memory device. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Additional embodiments of the present invention are listed hereinafter, without limitation. The embodiments provided for below are described as computer-implemented method claims. However, one of ordinary skill in the art would realize that the method steps may be embodied as computer code and the computer code could be placed on a nontransitory computer readable medium defining a computer program product.

Although the above discussion discloses various exemplary embodiments of the invention, it should be apparent that those skilled in the art can make various modifications that will achieve some of the advantages of the invention without departing from the true scope of the invention. For example, the patient could be an animal, in which case a human caregiver would make the medical decision.

What is claimed is:

1. A method, for use with at least one processor on at least one computer, of generating a report to help decide among a plurality of treatment options for a patient with a given treatable medical condition, the method comprising:

receiving patient information related to the patient and the medical condition;

querying a treatment option database to generate a plurality of potential treatment options for the medical condition;

receiving preference information indicative of the patient's preference for potential treatment outcomes of the treatment options to produce a preference value;

analyzing indexed study data relating to the plurality of treatment options by at least grading evidence within the indexed study data, wherein the indexed study data is derived from scientific studies, each of which evaluates an effect of a different treatment option on different trial subjects who have a similar medical condition as the patient;

producing a study score for each of the treatment options based on the analysis of the indexed data;

determining, for each distinct treatment option, a distinct treatment score as a function of at least the preference value and the study score corresponding to the distinct treatment option;

generating a report listing the treatment options and a) the treatment scores or b) information derived from the treatment scores.

2. The method as defined by claim 1 wherein the information derived from the treatment scores is a ranking of the treatment options as a function of the treatment scores for the treatment options.

3. The method as defined by claim 2, further comprising determining that a difference between a highest treatment score and a next highest treatment score is larger than a threshold, determining that no single value used to compute the highest treatment score is greater than the next highest treatment score or the value used to compute the next highest treatment score, and selecting a recommended treatment option with the highest treatment score.

4. The method as defined by claim 2, further comprising choosing two treatment options with the highest treatment scores;

determining if a difference between the two highest treatment scores falls below a pre-defined threshold, and if so, recalculating the treatment scores without using the preference value.

5. The method as define by claim 1, further comprising:

comparing the patient information with characteristics of trial subjects tested in at least one scientific study represented by the indexed study data to determine the applicability of at least one study to the patient, represented by an applicability value; and recalculating, for each treatment option, the treatment score as a function of the preference value, study score, and applicability value.

6. The method as defined by claim 1 further comprising:

receiving treatment recommendations from a plurality of experts, the treatment recommendations relating to the plurality of treatment options;

converting, at least in part in a computer process, the treatment recommendations into an expert score for each treatment option; and for each treatment option, recalculating the treatment score as a function of the preference value, study score, and expert score.

7. The method as define by claim 6, further comprising applying an expert weight to the expert score.

8. The method as defined by claim 7, wherein the expert weight is calculated using at least one of a ranking of the expert's academic institution, a ranking of the expert's employing institution, the expert's previous success in recommending, the expert's degree of experience, and the relatedness of the expert's qualifications or experiences to treating or working or processing conditions of the patient.

9. The method as defined by claim 1, further comprising storing, in an outcome database, treatment decisions by a plurality of patients together with medical outcomes of the treatments and reporting to the patient information derived from the outcome database related to past outcomes.

10. The method as defined by claim 9, further comprising determining the treatment scores as a function of the success rate in the outcome database.

11. The method as defined by claim 1 further comprising formulating a medical question, the question comprising patient information, information about the medical condition, and a list of the potential treatment options.

12. The method as defined by claim 11, further comprising sending the question to a panel of experts, receiving response information from the experts about treatment options and reporting the response information to the patient.

13. The method as defined by claim 1 further comprising creating the treatment option database.

14. The method as defined by claim 1 further comprising creating a database with the indexed study data.

15. The method as defined by claim 1, wherein each study score also corresponds to an effectiveness demonstrated by the treatment option in a distinct study.

16. A computer program product including a non-transitory computer-readable medium having computer code thereon for generating a report to help decide among a plurality of treatment options for a patient for a given treatable medical condition, the computer code comprising:
   computer code for receiving patient information related to the patient and the medical condition;
   computer code for querying a treatment option database to generate a list of potential treatment options for the medical condition; and
   computer code for receiving preference information indicative of the patient's preference for potential treatment outcomes of the treatment options to produce a preference value;
   computer code for analyzing indexed study data relating to the plurality of treatment options by at least grading evidence within the indexed study data, wherein the indexed study data is derived from scientific studies, each of which evaluates an effect of a different treatment option on different trial subjects who have a similar medical condition as the patient;
   computer code for producing a study score for each of the treatment options based on the analysis of the indexed data;
   computer code for determining, for each distinct treatment option, a distinct treatment score as a function of at least the preference value and the study score corresponding to the distinct treatment option; and
   computer code for generating a report listing the treatment options and a) the treatment scores or b) information derived from the treatment scores.

17. The computer program as defined by claim 16 wherein the information derived from the treatment scores is a ranking of the treatment options as a function of the treatment scores for the treatment options.

18. The computer program as defined by claim 17, further comprising
   computer code for determining that a difference between the highest treatment score and a next highest treatment score is larger than a threshold,
   computer code for determining that no single value used to compute the highest treatment score is greater than the next highest treatment score or the values used to compute the next highest treatment score, and
   computer code for selecting a recommended treatment option with a highest treatment score.

19. The computer program as defined by claim 17, further comprising
   computer code for choosing two treatment options with the highest treatment scores; and
   computer code for determining if a difference between the two highest treatment scores falls below a pre-defined threshold, and if so, recalculating the treatment scores without using the preference value.

20. The computer program as define by claim 16, further comprising:
   computer code for comparing the patient information with characteristics of trial subjects tested in at least one scientific study represented by the indexed study data to determine the applicability of at least one study to the patient represented by an applicability value; and
   computer code for recalculating, for each treatment option, the treatment score as a function of the preference value, study score, and applicability value.

21. The computer program as defined by claim 16 further comprising:
   computer code for receiving treatment recommendations from a plurality of experts, the treatment recommendations relating to the plurality of treatment options;
   computer code for converting, in a computer process, the treatment recommendations into an expert score for each treatment option; and
   computer code for recalculating, for each treatment option, the treatment score as a function of the preference value, study score, and expert score.

22. The computer program as define by claim 21, further comprising computer code for applying an expert weight to the expert score.

23. The computer program as defined by claim 22, wherein the expert weight is calculated using at least one of a ranking of the expert's academic institution, a ranking of the expert's employing institution, the expert's previous success in recommending, the expert's degree of experience, and the relatedness of the expert's qualifications or experiences to treating or working or processing conditions of the patient.

24. The computer program as defined by claim 16, further comprising computer code for storing, in an outcome database, treatment decisions by a plurality of patients together with medical outcomes of the treatments and computer code for reporting to the patient information derived from the outcome database related to past outcomes.

25. The computer program as defined by claim 24, further comprising computer code for determining the treatment scores as a function of the success rate in the outcome database.

26. The computer program as defined by claim 16 further comprising computer code for formulating a medical question, the question comprising patient information, information about the medical condition, and a list of the potential treatment options.

27. The computer program as defined by claim 26, further comprising computer code for sending the question to a panel of experts, and computer code for receiving response information from the experts about treatment options and reporting the response information to the patient.

28. The computer program as defined by claim 16, wherein each study score also corresponds to an effectiveness demonstrated by the treatment option in a distinct study.

29. A medical treatment recommendation system for generating a report to help decide among a plurality of treatment options for a patient for a given treatable medical condition comprising:
   a patient information receiving module executing on a computer that receives patient information related to the patient and the medical condition;
   a querying module executing on a computer that queries a treatment option database to generate a list of potential treatment options for the medical condition;
   a preference information receiving module executing on a computer that receives patient information indicative of the patient's preference for potential treatment outcomes of the treatment options to produce a preference value;
   an analysis module executing on a computer that analyzes indexed study data relating to the plurality of treatment options by at least grading evidence within the indexed study data, wherein the indexed study data is derived from scientific studies, each of which evaluates an effect of a different treatment option on different trial subjects who have a similar medical condition as the patient;
   a study score producing module executing on a computer that produces a study score for each of the treatment options based on the analysis of the indexed data;
   a treatment scoring module executing on a computer that determines for each distinct treatment option a distinct treatment score as a function of at least the preference value and study score corresponding to the distinct treatment option; and
   a reporting module executing on a computer that generates a report listing the treatment options and a) the treatment scores or b) information derived from the treatment scores.

30. The system as defined by claim 29 wherein the information derived from the treatment scores is a ranking of the treatment options as a function of the treatment scores for the treatment options.

31. The system as defined by claim 30, further comprising a module for determining that a difference between a highest treatment score and a next highest treatment score is larger than a threshold,
   a module for determining that no single value used to compute the highest treatment score is greater than the next highest treatment score or the values used to compute the second highest treatment score, and
   a module for selecting a recommended treatment option with the highest treatment score.

32. The system as defined by claim 30, further comprising a module for choosing two treatment options with the highest treatment scores, and
   a module for determining, if a difference between two highest treatment scores falls below a pre-defined threshold, and if so, recalculating the treatment scores without using the preference value.

33. The system as define by claim 29, further comprising:
   a module for comparing the patient information with characteristics of trial subjects tested in at least one scientific study represented by the indexed study data to determine the applicability of at least one study to the patient represented by an applicability value; and
   a module for recalculating, for each treatment option, the treatment score as a function of the preference value, study score, and applicability value.

34. The system as defined by claim 29 further comprising:
   a module for receiving treatment recommendations from a plurality of experts, the treatment recommendations relating to the plurality of treatment options;
   a module for converting, in a computer process, the treatment recommendations into an expert score for each treatment option; and
   a module for recalculating, for each treatment option, the treatment score as a function of the preference value, study score, and expert score.

35. The system as define by claim 29, further comprising a module for applying an expert weight to the expert score.

36. The system as defined by claim 35, wherein the expert weight is calculated using at least one of a ranking of the expert's academic institution, a ranking of the expert's employing institution, the expert's previous success in recommending, the expert's degree of experience, and the relatedness of the expert's qualifications or experiences to treating or working or processing conditions of the patient.

37. The system as defined by claim 29, further comprising a module for storing, in an outcome database, treatment decisions by a plurality of patients together with medical outcomes of the treatments and reporting to the patient information derived from the outcome database related to past outcomes.

38. The system as defined by claim 37, further comprising a module for determining the treatment scores as a function of the success rate in the outcome database.

39. The system as defined by claim 29 further comprising a module for formulating a medical question, the question comprising patient information, information about the medical condition, and a list of the potential treatment options.

40. The system as defined by claim 39, further comprising a module for sending the question to a panel of experts, receiving response information from the experts about treatment options and reporting the response information to the patient.

41. The system as defined by claim 29, wherein each study score also corresponds to an effectiveness demonstrated by the treatment option in a distinct study.

* * * * *